(12) United States Patent  
Weinberg et al.

(10) Patent No.: US 7,959,592 B2  
(45) Date of Patent: *Jun. 14, 2011

(54) TUBULAR COMPRESSIVE DEVICE AND METHODS OF USE RELATING TO SAME

(75) Inventors: Paul N. Weinberg, Los Angeles, CA (US); Yvette B. Scherpenborg, Santa Monica, CA (US)

(73) Assignee: Therogel, Inc., Newbury Park, CA (US)

( * ) Notice: Subject to any disclaimer, the term of this patent is extended or adjusted under 35 U.S.C. 154(b) by 411 days.

This patent is subject to a terminal disclaimer.

(21) Appl. No.: 12/060,052

(22) Filed: Mar. 31, 2008

(65) Prior Publication Data

US 2008/0183118 A1    Jul. 31, 2008

(51) Int. Cl.
*A61F 5/00* (2006.01)
*A61F 13/00* (2006.01)

(52) U.S. Cl. ............... 602/62; 602/20; 602/23; 602/41; 602/60; 602/63; 602/64

(58) Field of Classification Search ............ 607/96, 607/108–112; 602/2, 20, 23, 26, 60–64
See application file for complete search history.

(56) References Cited

U.S. PATENT DOCUMENTS

| | | | |
|---|---|---|---|
| 3,425,412 A | 2/1969 | Pope | |
| 3,473,527 A * | 10/1969 | Spiro | ............... 602/26 |
| 4,516,572 A | 5/1985 | Schlein | |
| 4,556,055 A | 12/1985 | Bonner, Jr. | |
| 4,588,400 A | 5/1986 | Ring et al. | |
| 4,592,358 A | 6/1986 | Westplate | |
| 5,160,328 A | 11/1992 | Cartmell et al. | |
| 5,190,033 A | 3/1993 | Johnson | |
| 5,267,952 A | 12/1993 | Gardner | |
| 5,334,646 A | 8/1994 | Chen | |
| 5,431,622 A | 7/1995 | Pyrozyk et al. | |
| 5,527,265 A | 6/1996 | McKeel | |
| 5,531,670 A | 7/1996 | Westby et al. | |
| 5,697,328 A | 12/1997 | Hunter | |
| 5,697,961 A | 12/1997 | Kiamil | |
| 5,887,437 A | 3/1999 | Maxim | |
| 5,994,450 A | 11/1999 | Pearce | |
| 6,287,269 B1 * | 9/2001 | Osti et al. | ............... 602/62 |
| 6,528,696 B1 | 3/2003 | Ireland | |
| 7,351,217 B2 * | 4/2008 | Scherpenborg | ............... 602/75 |
| 2002/0103520 A1 | 8/2002 | Latham | |
| 2007/0255189 A1 * | 11/2007 | Halanski et al. | ............... 602/8 |

* cited by examiner

*Primary Examiner* — Kim M Lewis
(74) *Attorney, Agent, or Firm* — Cotman IP Law Group, PLC (57) ABSTRACT

A lightweight, flexible, aerating, compressive, thermal material. Perforations allow the treatment area to aerate. Thermal capacity of the invention allows for hot or cold treatment in a manner that compressively supports the object undergoing thermal treatment while maintaining maximum mobility. The material is made from an elastomer such as polyurethane with the addition of silicon and vegetable oil. Resin is used to color the product.

8 Claims, 7 Drawing Sheets

TUBULAR COMPRESSIVE DEVICE AND METHODS OF USE RELATING TO SAME

This application claims the benefit of U.S. Provisional Patent Application No. 60/970,887 filed Sep. 7, 2007, the specification of which is hereby incorporated herein by reference. This application is also a continuation-in-part to U.S. application Ser. No. 10/848,963 filed May 19, 2004 which claims the benefit of U.S. Provisional Patent Application Ser. No. 60/320,215 filed May 23, 2003, both of which are hereby incorporated herein by reference.

BACKGROUND OF THE INVENTION

Embodiments of the invention relate to the field of medical devices and more particularly to solid elastomers applied to an area of discomfort for purposes of heating or cooling the area, providing compression to the area, aerating the area, and/or providing padding to the area. No existing device provides such a combination of affects to provide optimal functionality and use for the wearer.

It is commonplace for people to utilize devices with thermal capacitance to treat an injury or area of discomfort. A hot-cold pack is an example of one such widely utilized device. Cold packs are generally used in order to numb an area and relieve swelling, while hot packs are used to loosen up tight muscles or tendon strains. Many hot-cold packs utilize a gelatinous substance that can undergo state changes in order to provide a higher capacity of heat absorption, i.e., cooling. Such gels may provide similar functionality using water or chemical compounds that initiate changes in state (i.e., liquid to solid). A majority of hot-cold packs and other similar devices store the gel or liquid based substance that provides thermal capacitance in a sealed bag. A problem with this approach is that over time, these bags often leak or otherwise degrade to a point where use is impractical.

Another issue with using current hot-cold packs is that problems can arise when the treatment area receives little air, as the underlying area can become sweaty and the hot-cold pack can laterally or vertically slide around on the treatment area during movement of the recipient. Thus, in some instances application of the hot-cold pack can further aggravate the injury, or frustrate the wearer to the point of not using the hot-cold pack.

Existing hot-cold packs are designed for use on immobile subjects and generally lack an effective securing mechanism. When the subject of the hot-cold pack treatment is an athlete, animal or a young child or any other entity requiring continued mobility, it is important to adequately secure the pack to the subject. Securing the hot-cold packs is typically achieved by a secondary means. Generally, the packs are held in place with an elastic bandage which limits the mobility of movement of recipient of the pack since the pack may easily become displaced and fall off. In other instances, the packs are held in place within a pouch that acts as a means for immobilizing and securing the pouch to a subject, however the packs are still heavy and even if secured tightly still inhibit mobility due to their weight and thickness.

In certain instances it is desirable to compress the hot-cold pack against the region of treatment. Current hot-cold packs lack the elasticity required to perform such compression. It is, however, possible to use a secondary means, namely by an elastic bandage wound around the hot-cold pack, to compress the hot-cold pack against the region to be treated. Thus, some compression type inventions require a secondary device in order to use the hot-cold pack. This is inconvenient in that a person wishing to apply the hot-cold pack to an area for treatment is required to utilize two items before application of the hot-cold pack can occur. In addition, the elastic properties of straps are known to degrade over time, resulting in a poor compression as the age of the strap increases.

The bandage described in U.S. Pat. No. 5,160,328, filed Nov. 3, 1992 to Cartmell, et al., entitled "Hydrogel bandage" consists of a self-adhesive bandage including a substrate having a two sides and multiple layers including a backing layer which forms the first side of the substrate, and an adhesive layer which forms the second side of the substrate. A hydrogel layer is disposed over the second side of the substrate and is made from a polyurethane hydrogel material for absorbing bodily fluids, including wound exudate. Multiple support layers may be interposed between the substrate and the hydrogel layer to provide the bandage with additional support. Although lightweight, and providing a means for aerating a wound, the bandage is incapable of providing compressive means to bear on the wound since the adhesive layer locks the bandage in place over a treatment area.

The bandage described in U.S. Pat. No. 5,531,670, filed Jul. 2, 1996 to Westby, et al., entitled "Heat Conserving Bandage" consists of a heat conserving bandage to cover human or animal tissue, comprising heat reflecting means, positioned next to the tissue for reflecting heat from the tissue, insulation material means covering said heat reflecting means, and cloth covering the insulation material. The heat reflecting means includes a sandwiched structure of a foil of plastic material adjacent to the tissue, and a second foil bonded thereto. Further cloth means can be inserted between the heat reflecting means the tissue. Suitably, the cloth means and the heat reflecting means are bonded together by sewing or an adhesive to create a pocket for receiving the insulation material. Although lightweight and flexible, the invention described provides no means for aerating the treatment area, and indeed attempts not to aerate a treatment area since it is providing a means to insulate only, and not add or remove heat.

The compress described in U.S. Pat. 4,556,055, filed Dec. 3, 1985 to Bonner, entitled "Cold Compress", consists of a bandage defined by a layer of closed cell foam polymeric material sandwiched between and bonded to adjacent layers of fabric. One of the layers of fabric is absorbent with respect to aqueous liquids, such as wound exudate, and is adapted to be in contact with an area of the body. Multiple straps are releasably attached to the bandage to form a compress. The straps facilitate adjustment of the compress, the compress also may possess elongated pockets sewn to the fabric layer opposite the absorbent layer for insertion of straps to form a brace or provide for additional cooling. Electrodes are contemplated for providing electrical stimulation. Although allowing for application of a cold pad on a treatment area with a compress, the invention is heavy, thus compromising mobility, and is cloth wrapped in order to absorb aqueous fluids. The bandage also allows for electrical stimulation.

The pad described in U.S. Pat. No. 4,588,400, filed May 13, 1986 to Ring, et al., entitled "Liquid loaded pad for medical applications", consists of wound and burn dressings which are prepared from pellicles, which are a thin film of microbially-produced cellulose obtained, for example, by culturing *Acetobacter xylinum*. A pellicle having a thickness from about 0.1 to 15 millimeters or greater is processed to replace the culture medium with water or other physiologically compatible liquid. The liquid-loaded pellicle is sterilized prior to its use as a dressing or in other medical applications. The pad is liquid based, is heavy, and therefore does not allow for complete mobility or direct aeration. It also appears to be directed towards immobile burn victims, hence it is not designed to provide a compressive means.

The therapeutic cooling device described in U.S. Patent Application 20020103520, filed Aug. 1 ,2002 to Latham, entitled "Therapeutic cooling devices", consists of a thermal regulatory system to reduce swelling caused by trauma to a variety of tissues and limbs. One or more substantially flexible, at least partially thermally conductive housings containing an activatable thermal regulatory medium may be coupled with one or more applicator, such as a splint, that is adapted to apply the thermal source to the tissue. The invention also discloses methods of therapeutically regulating tissue temperature. The invention relates to thermal regulatory systems that are generally heavy gel filled devices that are form fitted for a particular body part not allowing mobility, and providing no means for compressing a treatment area.

The therapeutic pack described in U.S. Pat. No. 5,190,033, filed May 2, 1993 to Johnson, entitled "Ice peas cold/hot therapeutic pack", consists of an improved cold/hot pack for physiotherapy having a completely sealed flexible pouch. The cavity of the pouch is filled with a plurality of approximately pea sized or larger hollow capsules. The cavities of the hollow capsules are filled with cold/hot storing fluid or gel and are essentially used as a replacement for frozen peas. Partitions prevent migration of the capsules within the pouch and a screened plug permits air to be expelled from the pouch while the capsules are retained in order to conform the pouch to a given body part. The invention appears to be flexible but contains capsules in a pouch that would inhibit mobility when the pouch was strapped on. In addition, the invention would not allow the underlying treatment area to be aerated. The invention appears have no means for applying a compressive force and is directed mainly to cooling of the treatment area solely in a manner mirroring the use of frozen vegetable bags.

The therapeutic device described in U.S. Pat. 4,592,358, filed Jun. 3, 1986 to Westplate, entitled "Therapeutic device", consists of a therapeutic device featuring a plurality of compartments enclosing a therapeutic substance such as a refrigerant material which remains a liquid or forms a slush at temperatures below about 0 degree Celsius, or a heat releasing substance, or a high density material which may be firmly positioned on various body portions using one or more strap means. The invention does not allow for aeration of an underlying treatment area, and uses liquid in order to cool, or a high density material to heat. Each mode of use would not allow for mobility or compression since the device provides non-elastic straps for fastening the device. The device can not be cut or formed into a shape other than that supplied.

The compress described in U.S. Pat. No. 5,697,961, filed Dec. 16, 1997 to Kiamil, entitled "Compress for use in cold and/or hot treatment of an injury", consists of a compress suitable for use in hot and cold treatments of an animal or human body part, comprising a flexible container containing a formulation comprising an aqueous solution and discrete particles of a crosslinked, water-absorbing polymer. In one embodiment, the compress is contained in a sealed plastic bag. The formulation used in the compress can be an antifreeze agent, a salt compound, a glycol compound or mixtures thereof. The crosslinked, water-absorbing polymer in one embodiment is polyacrylamide or sodium polyacrylate. The invention applies a compressive force to a treatment area, but does not allow for aeration, is heavy, can require an external heat storage unit attached to the compress and is therefore unable to provide mobility. In addition the device cannot be cut to fit a treatment area.

The bandage described in U.S. Pat. No. 5,431,622, filed Jul. 11, 1995 to Pyrozyk et al., entitled "Thermal bandage", consists of a thermal bandage apparatus for simultaneously dressing and thermally treating a wounded area. The device includes a fluid absorbent member having a wound contacting surface for absorbing bodily fluids produced by an open wound and a holding means adjacent and connected to the fluid absorbent member for holding a thermal medium against the fluid absorbent member such that heat is transferred between the thermal medium and the open wound by thermal conduction through the fluid absorbent member. There is also disclosure of an arrangement for providing a continuous supply of heat or cold to a wound. The invention is a non-aerating, and fluid absorbing bandage with associated thermal source pump attached or pouches for the insertion of gel bags. The invention, therefore, does not allow for mobility, aeration or compression.

The bandage described in U.S. Pat. No. 5,887,437, filed Mar. 30, 1999 to Maxim, entitled "Self-adhering cold pack", consists of a self-adhering cold pack having an envelope defining a sealed cold pack volume. A cooling agent is positioned in the cold pack volume. A bandage sheet is fixed to the envelope by a bandage adhesive. The bandage sheet defines mounting tabs linearly extending from the envelope outer perimeter in order to support a bandage adhesive for temporary adhesion of the cold pack to the skin surface of a patient. The invention does not allow for aeration, is heavy and would not allow for compression of the treatment area.

The bandage described in U.S. Pat. No. 6,528,696 filed Mar. 4, 2003, to Ireland, entitled "Pliable contact bandage", consists of a pliable contact bandage for placement over a wound site located on any skin surface. The apparatus includes a re-openable, flexible enclosure adapted to receive a source of heat or cold, and an adhesive for mounting the pliable contact bandage on a skin surface. The source of heat or cold is temporarily placed within the flexible enclosure and the pliable contact bandage is placed over the wound site in a heat conducting relationship. Typically, a hypo-allergenic adhesive is located along at least a portion of the periphery of the flexible enclosure. The periphery of the flexible enclosure surrounds the wound site. There is no attempt made at enabling mobility or aeration, or compression of the treatment area.

The elastomer described in U.S. Pat. No. 5,334,646, filed Aug. 2, 1994, to Chen, entitled "Thermoplastic elastomer gelatinous articles", consists of novel gelatinous compositions and articles formed from an intimate melt blend admixture of poly(styrene-ethylene-butylene-styrene) triblock copolymer and high levels of a plasticizing oil. The gelatinous composition is transparent and has properties including unexpectedly high elongation and tensile strength and excellent shape retention after extreme deformation under high-velocity impact and stress conditions. The gelatinous products of this invention are soft, flexible, and have elastic memory, characterized by a gel rigidity of from about 20 gram to about 700 gram Bloom. The invention is an elastomer and articles of manufacture based on the gelatinous elastomer. The patent however does not enable the creation of an aerating, mobile embodiment, or enable the manufacture of an embodiment with additives allowing for higher heat capacity.

The elastomer described in U.S. Pat. No. 5,994,450, filed Nov. 30, 1999, to Pearce, entitled "Gelatinous elastomer and methods of making and using the same and articles made therefrom"consists of gelatinous elastomers, methods for making gelatinous elastomers, methods for using gelatinous elastomers, products made from gelatinous elastomers, and products which include gelatinous elastomers as a component or ingredient. More particularly, the invention includes a gelatinous elastomer formed from a combination of a block copolymer of the general configuration A-B-A and a plasticizer. The preferred A-B-A copolymer of the invention is polystyrene-hydrogenated poly(isoprene+butadiene)-polystyrene and the preferred plasticizer is either mineral oil or a combination of mineral oil and resin. Various other components may be included in the preferred recipes according to the invention. This invention includes improvements to Chen's '646 invention, but does not enable the construction of a lightweight, aerating, mobile, compressive bandage.

Because of the problems associated with current systems, there is a need for an improved bandage that adequately overcomes the limitations existent in the prior art.

BRIEF SUMMARY OF THE INVENTION

Embodiments of the invention are directed to a support device that comprises a flexible thermal capacitive elastomer configured for use as a bandage and/or to provide compression, padding and/or insulation. The elastomer is designed to retain alterations in temperature so that when applied to an area in need of treatment it changes the temperature of that area while simultaneously aerating and allowing for padding and compression to be applied to the area under treatment. Such abilities are achieved in accordance with one or more embodiments of the invention by molding the material into a planar or other form that comprises a set of interspersed perforations that increase the devices' elasticity and "grip", (i.e., the traction of the bandage against the treatment area), while allowing for aeration of the treatment area. The device is however not limited to a particular shape and is intended for use in any dimension that has a suitable purpose. In some instances it is beneficial to vary the total surface area of the material so that the material effectively covers the treatment area.

To provide compression to specific parts of the body various shapes that conform to various appendages are contemplated. An adaptation for example that is formed in the shape of an open ended tube having a circumference that differs based on the appendage for which the compressive bandage is to be used is within the scope and spirit of the invention. The area targeted for application generally dictates the shape and circumference of the compressive bandage. In one embodiment of the invention users of the device can adjust the size by cutting the elastomer material into any desired shape. Since the material that makes up the device is solid there are no leakage problems of the sort that exist with existing medical cold or hot press type devices. It is possible to increase or decrease the material's heat capacitance by adjusting the thickness to suit the intended use. Also, the thicker and wider the material, the more force required to change the shape. Since the device makes use of a flexible material, the problems existent in the prior art, namely rupturing and other forms of degradation, are overcome.

To provide more or less air flow to the area subject to treatment, the material may contain a set of interspersed perforations that vary in size and quantity. The perforations may take any shape or arrangement that allows air to flow to the treatment area. The perforations may, for instance, be geometric or customized to take advantage of a particular niche market. In instances where the target market is identifiable, the perforations may take a form suitable for that market. If, for example, the bandage was intended for use in a children's hospital the perforations (and/or shape of the bandage itself) may take the form of a popular cartoon or other such character. Company logos or interesting patterns might also be used to provide further interest to the material itself.

One or more embodiments of the invention enable improved mobility while the device is in use. The material may, for instance, contain an adhesive end, VELCRO® attach areas or male extrusions that fit or snap into the perforations in order to secure the bandage to the treatment area while maintaining a compressive force and still allowing aeration of the area being treated. The material also provides insulation and padding in instances where it might be desired. In the tube embodiment fastening mechanisms are not required but may be optionally provided to increase the compressive force if desired. Readers should note, however, that the invention is not limited to these specific attachment means and contemplates the use of any mechanism able to limit movement of the bandage when applied to the treatment area.

Various applications of the support device are contemplated and thus the device may be used in contexts where it is beneficial for the wearer to have an appendage in contact with the elastomer material. A sock, for example, that is formed of the elastomer material and worn to provide compressive treatment, comfort or insulation is one possible implementation. The size and shape of the sock is modified to fit the appendage it is intended for use with. One size for instance might be shaped and sized for use on feet and thus have application in conjunction with footwear such as shoes or ski boots. When used in this context the elastomer material provides the user with insulation and padding beyond that provided by the shoe itself. The same general concept, that being that the material applied around and appendage can provide insulation and padding is applicable to others sorts of apparel or medical devices as well. The material may, for instance be woven into or made part of bandages, splints, or even basic clothing apparel where additional padding is beneficial such as in the context of sports or for those who have an injury that is made more comfortable through the use of additional padding or compression to the area of injury.

Embodiments of the invention enable a material configured to enable application of compressive force to an appendage while simultaneously aerating said appendage, said material comprising a flexible tubular element formed from an elastomer based substance, a plurality of perforations protruding through said flexible tubular element where each of said plurality of perforations is for purposes of aerating said appendage and increasing said flexible planar element's ability to grip said region of said human being undergoing treatment. The material may further comprise a housing for said material. The housing may comprise a shoe. The housing may comprise a medical device. The housing may comprise apparel. The material may further comprise inserts into said flexible tubular element to enable a subject wearing said flexible tubular element to change the shape of said flexible tubular element. The elastomer based substance may change color depending upon a temperature associated with said flexible tubular element. The size of said tubular element may be varied through a sizing element.

BRIEF DESCRIPTION OF THE DRAWINGS

The above and other aspects, features and advantages of the invention will be more apparent from the following more particular description thereof, presented in conjunction with the following drawings wherein.

DETAILED DESCRIPTION

A tubular compressive device and methods of use relating to same will now be described. In the following exemplary description numerous specific details are set forth in order to provide a more thorough understanding of embodiments of the invention. It will be apparent, however, to an artisan of ordinary skill that the present invention may be practiced without incorporating all aspects of the specific details described herein. In other instances, specific features, quantities, or measurements well known to those of ordinary skill in the art have not been described in detail so as not to obscure the invention. Readers should note that although examples of the invention are set forth herein, the claims, and the full scope of any equivalents, are what define the metes and bounds of the invention.

Embodiments of the invention are directed to a crosslinked high-polymer materials with elastic behavior (e.g., an elastomer) formed for use as a compression wrap. The material that makes up the wrap is designed to retain alterations in temperature so that when applied to an area in need of treatment the wrap effectuates a change in temperature to that area while simultaneously aerating and allowing for compression to be applied. Thus, the material used to implement one or more aspects of the invention provides a mechanism for cooling or heating an area of a person or animal that has been injured or is in discomfort. In addition to affecting changes in temperature to an area the device is also adaptable for use for purposes of providing compression to a person or animals appendage and/or insulation or padding in cases where that is desired to increase comfort.

In the case where a user wishes to cold treat an area, the user can cool the device by exposing the elastomer material to a refrigerated environment for a duration of time adequate enough to bring the material's temperature to a level sufficient for the intended use. Once the material is at an appropriate temperature, the user may apply it to the desired area for purposes of cooling that area. Conversely, by placing the material in warm or hot water, the user may apply the bandage to the desired area for purposes of warming that area. One major advantage of using a gel like material such as an elastomer for the device is that the temperature of the gel is manageable and does not get uncomfortably cold for the wearer. This avoids the problem ice packs and other chemical based cold materials have in that they get so cold they cannot be put in contact with the skin without causing discomfort or freezer burn. Because of the elastic properties of the material, users can optionally utilize the device to tightly wrap the area being treated and thereby simultaneously apply compression and cold or hot treatment to that area. The solid material retains its elasticity in hot or cold applications and can provide compression in either situation. The material can also be used as a source for applying aerated compression, padding and/or insulation without the need to effectuate changes in the material's surface temperature. In one embodiment of the invention the material is treated with a chemical that permits the color of the material to alter based on a temperature suited for a specific treatment. When the material is adequately cooled for instance, it may have an appropriate color of blue and when the material is heated it may turn yellow. If heated to a temperature that may cause burns or is inappropriate for the desired treatment the material may become red or any other suitable color. The concept of correlating a color to a specific temperature range and then varying the color based on the temperature is not color specific and hence any color may be used in conjunction with a specific range.

Figure 1:
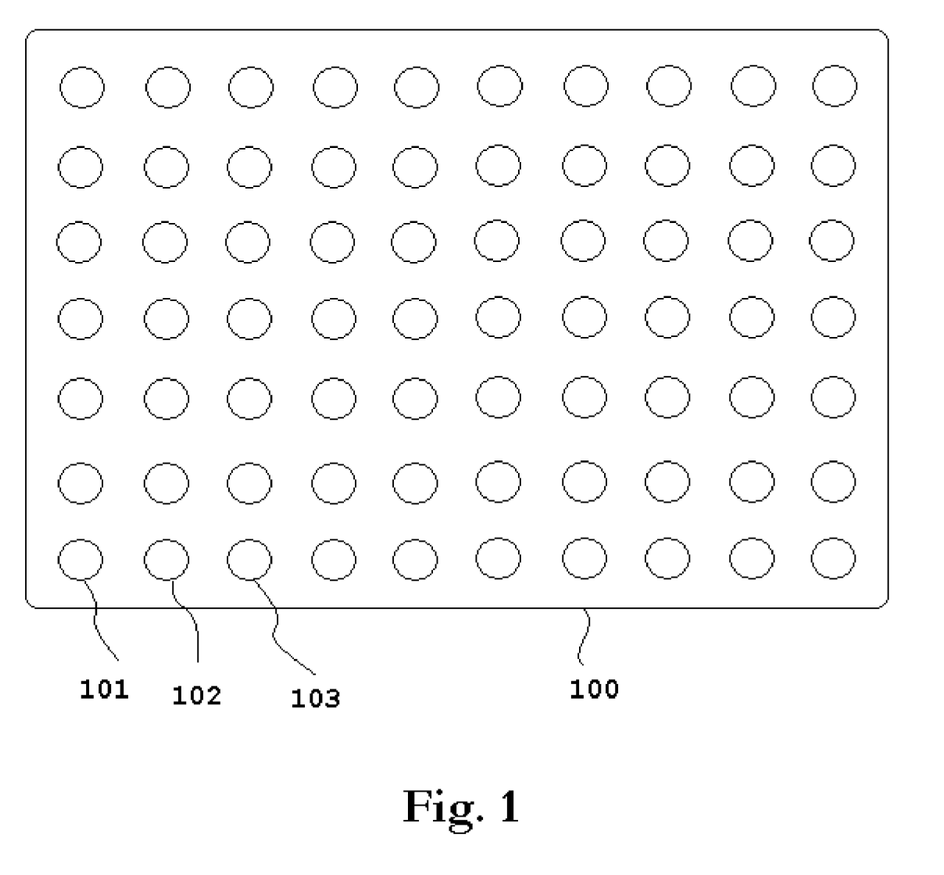
FIG. 1 is a top view of a material configured to aerate a treatment area in accordance with an embodiment of the invention.

FIG. 1 depicts an example configured in accordance with an embodiment of the invention for use as a compressive wrap. In the example illustrated, the flexible material is molded into a planar form 100 that comprises a set of interspersed perforations 101, 102, 103 designed to increase or maintain elasticity while allowing for aeration of the area subject to treatment and compression. In one embodiment of the invention the planar form is achieved via an injection mold process that utilizes an elastomer material (e.g., a polyurethane with the addition of silicon and vegetable oil) having properties of thermal capacitance and adequate elasticity. It is important, however, that readers be cognizant of the fact that it is feasible to implement embodiments of the invention using many different types of elastomers or other compounds and that as such embodiments of the invention include, but are not limited solely to polyurethane elastomers.

It is advantageous to utilize the planar form because such a shape maximizes the surface area able to contact the treatment area. However, the invention also contemplates the use of other dimensions and can take any shape, thickness, and size suitable to meet a particular need. For instance, by using a cutting implement (e.g., scissors, a box cutter, knife, etc. . . . ) users may cut the planar form into any shape for purpose of making the fits against the area of treatment more comfortable. Perforations in the material may act as a guide for cutting and users may save material cut away from the planar form for later use in the same of different context. The thickness of the material can vary from thinner than 1 mm, to thicker than 25 mm, in order to provide solutions for different treatment types. For example a wrap for a wrist could be less than 5 mm thick, while the thickness for an animal leg could be over 25 mm thick.

The invention also contemplates the implementation of three-dimensional configurations molded to fit comfortably against or around a body part. To provide compression to specific parts of the body various shapes that conform to various appendages are contemplated. An adaptation for example that is formed in the shape of an open ended tube having a circumference that differs based on the appendage for which the compressive bandage is to be used is within the scope and spirit of the invention. The area targeted for treatment generally dictates the shape and circumference of the compressive bandage. A tube fitted to surround a part of a leg or arm is for instance a different size depending upon whether the tube is to be applied to an arm or leg. In cases where the target for compression treatment is an ankle the shape of the tube may take the form of a sock or other tubular type shape with a closed or open end that surrounds the ankle region and provides the desired compression and ability to apply varying temperatures to the region under treatment by cooling or heating the material. The sock may them be adapted for use in show, boots or other sports related footwear that benefits by giving the wearer increased padding, insulation and/or compression. The inner and outer material of the sock may vary based on application so as to minimize friction when putting the sock or tubular embodiment on the wearer. A cloth, nylon or other material may surround the elastomer itself so that the gel does not grip the footwear when being inserted by the wearer. In other cases the elastomer is incorporated into a sports related device such as a shoe, glove, elbow pad, or kneepad and the material is one of multiple layers where the layer in contact with the skin comprises a second material designed to minimize friction when the wearer inserts or removes an appendage.

Tubular shapes that conform to other appendages or regions of the body in need of aerated compression, temperature change, insulation and/or padding are also feasible and hence the invention may be adapted for use to surround a finger, hand, wrist, elbow, shoulder, knee, back or any other part of the body where compressive treatment is desired. In one embodiment of the invention a glove is made to fit around a subjects hand and provide aerated compression and/or the ability to apply hot and/or cold treatment to the subject's hand region while padding and insulating the region. The material may also take a tubular shape that functions as a sleeve for purposes of it being applied to a wrist or elbow area. Tubular embodiments of the invention are generally sized as appropriate for the intended appendage and may also contain curvatures or inserts within the material to make the bandage shapeable by the wearer to improve comfort and/or apply more or less compression to an area. The insert may take various forms that provide wearers with the ability to custom shape the bandage for maximum comfort. For instance, a wire or flexible plastic that wraps around the appendage may provide the mechanism for changing the shape of the bandage to better conform with the area of treatment. In other cases the material is used to improve comfort for devices configured to restrict or immobilize a body part such as a splint, brace, and/or cast. A sock shaped embodiment has application for purposes of providing not only compression but also insulation and padding when used in forms where the sock surrounds an appendage or joint such as an ankle, wrist, elbow, knee or fingers.

The planar or tubular forms of the device described herein may be utilized in tandem with other treatments, devices or apparel so as achieve improved comfort for the wearer. When sized appropriately for a specific appendage the tubular shape can be inserted into shoes, formed as a sock or used inside or in conjunction with clothing apparel or sports devices for added comfort and wearability. Utilizing the invention in tandem with another method of treatment, such as a larger general purpose bandage, or splint, that provides for the addition of compression and thermal treatments is also contemplated. In this instance for example the tubular embodiment of the invention could be integrated into a bandage or splint so as to provide aerated compression to the area of treatment. Also in one embodiment where the invention is used in the lining of apparel, where the invention is removable from apparel and can be adjusted for heat control but is then reinserted via a holding mechanism such as a pouch, pocket, or VELCRO® fastener. The material also has uses as a joint support unit such as those used for sore elbows and knees to provide compression, thermal treatment or comfort.

In one embodiment of the invention, the planar or tubular form is composed of a biodegradable compound having a minimal or no toxic effect. Reuse is possible simply by rewashing the material. Storage is simplified because it is possible to keep the material in the refrigerator or freezer, or stored at room temperature and placed in ice water for quick preparation for cold pack treatment. To use the material as a heat pack, a user may fill a hot bucket with water and submerse the material into the water.

Figure 2:
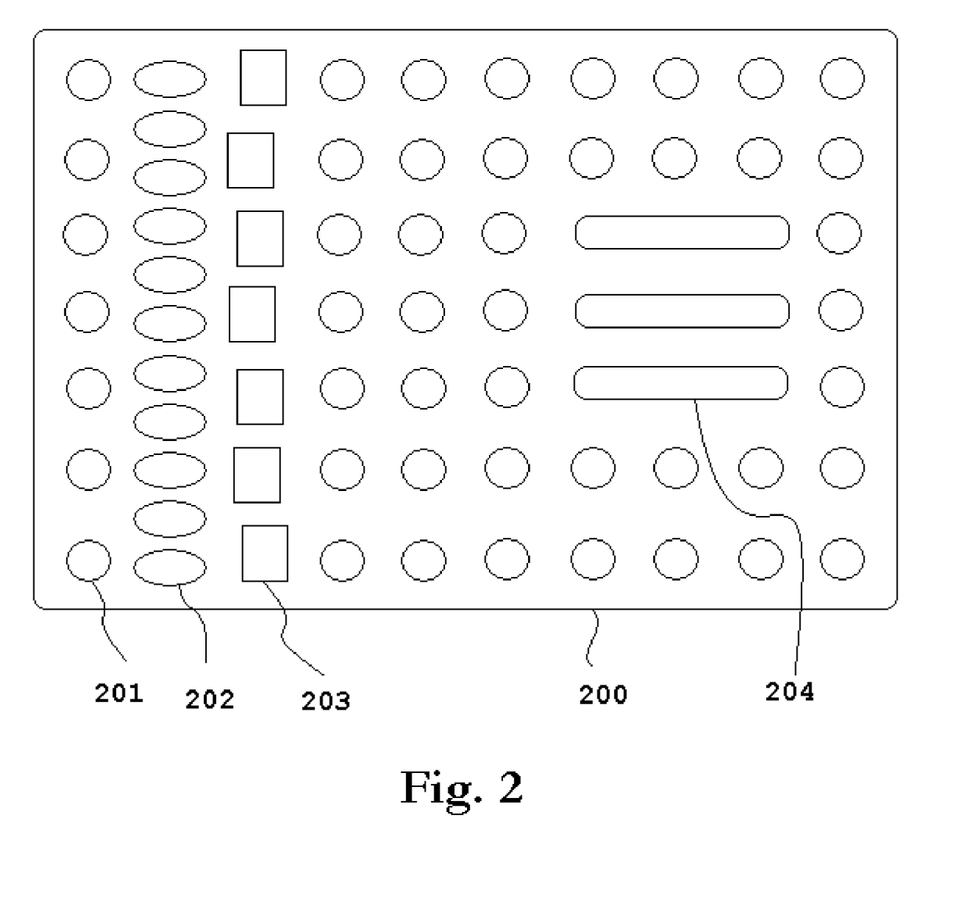
FIG. 2 illustrates an embodiment of the invention with non-uniform placement of perforations.
Figure 3:
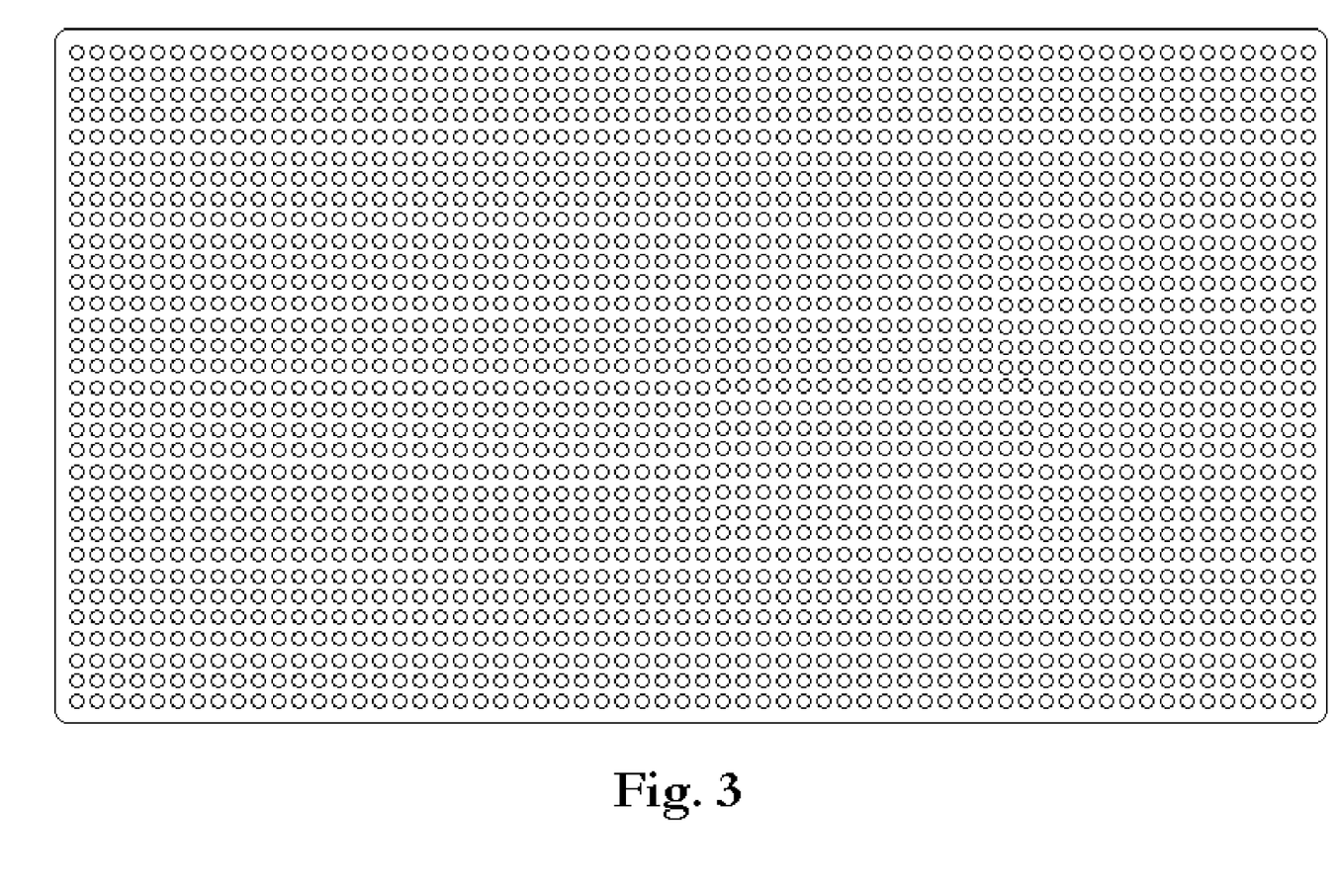
FIG. 3 is a perspective view of an embodiment with male extrusions that fit into the perforations for securing purposes

The planar or tubular form contains a set of interspersed perforations 100 that can vary in size and quantity while still providing some level of airflow to the area of treatment. For instance, embodiments of the invention contemplate the use of perforations placed closely or as far away from one another as the particular application requires. Thus, the material may contain a set of uniformly or non-uniformly spaced perforations that have consistent or inconsistent diameters and proximity to one another. FIG. 1 illustrates a set of uniformly spaced perforations having consistent diameters whereas FIG. 2 illustrates a set of non-uniformly spaced perforations 201, 202, 203 and 204 having inconsistent shapes, sizes and locations. In instances where aeration of the treatment area is paramount, the material may contain bigger perforations than in instances where aeration is less important. The perforations can also have varying shapes and may, for instance, be geometric or customized to take advantage of a particular niche market. In instances where the target market is identifiable, the perforations may take any shape suitable for that market. If, for example, the material was intended for use in a children's hospital the perforations (and/or shape of the material itself) may take the form of a popular cartoon or other such character.

Figure 5:
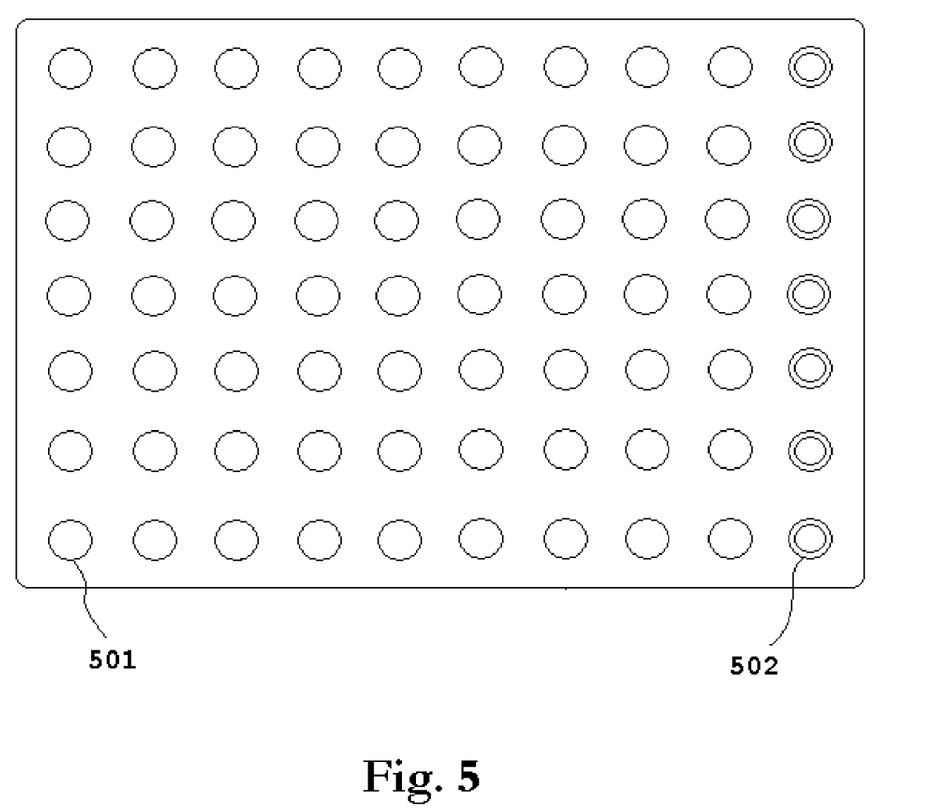
FIG. 5 illustrates an embodiment of the invention for use as an equestrian saddle pad.

FIG. 5 shows an embodiment of invention configured to secure the material into a fixed position over the treatment area or extend the material to cover a larger surface area. For instance, it is possible to fasten or hook the material into longer chains by using snaps 502 that fit into perforations 501. The invention is however not limited explicitly to the use of snaps and contemplates the use of any other type of fastening device able to provide a way to couple materials together or secure them in place over the treatment area. In other instance, the securing mechanism provides a way to consistently apply a certain amount of compression to the treatment area.

Exemplary Methods of Use

Embodiments of the invention are applicable for a wide number of uses. Some, but not all of these uses are discussed below for purposes of example. Since it is possible to manufacture the invention in virtually any shape or size the material has applicability in any instance where aeration, compression, padding, insulation and/or cooling or heating of a surface area is desired. A sunburned person, for instance, might use the material as a blanket or for application to a specific body part that is particularly sunburned. By placing the blanket-sized embodiment in a freezer or refrigerator, users can cool the material and then wrap it around the patient, thereby providing a soothing relief to the painful effects of the burn.

An embodiment of the invention also has uses as a heat source for someone suffering from cold exposure. For instance, placing a blanket size embodiment in a tub of hot water can act as a means for preheating the blanket prior to arrival of an exposure victim. Once the victim arrives, users can remove the blanket sized embodiment from the water, roll the blanket in a towel to dry it, and wrap the blanket around the victim. Such an implementation enables the victim's skin to breath while maintaining warmth. Wrapping the victim inside a sleeping bag or towel provides further insulation from any environmental temperature effects. It is also possible to use the material to compression wrap injured limbs with elements cut from the main blanket, or with independently heated or cooled sections. By compressing the material over portions of the body, direct contact of the heated bandage can quickly warm the body and bring the victim out of shock.

FIGS. 7A-7D illustrate a tubular embodiment of the invention for use in various contexts. The tubular embodiment of the invention is configured for use to surround an appendage of a human or animal for purposes of providing aerated compression, insulation and/or padding. The perforations 701 provide increased airflow to the area of treatment. The size of the tubular element is variable depending on the wearer. To vary size tubes are made with different circumferences determined based on the anticipated size of the wearer and the specific appendage for which the device is intended. To vary the size different circumference tubes may be manufactured or the device may contain a sizing element 702 that enables it to be adjusted based on the person or animal using the device. The sizing element may take various forms in order to adjust the fit of the tubular element. The sizing element may for instance, comprise VELCRO® that surrounds the tube and when adjusted increases or decreases the tightness of the device. The sizing element may also use a mesh, wire, string or other such element embedded inside or external to the tubular element that when pulled tight or relaxed changes the circumference of the device.

Figure 7A:
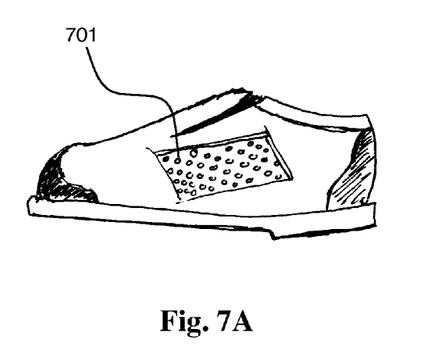
FIG. 7A, 7B, 7C, and 7D illustrate a tubular embodiment of the invention for use in various contexts.
Figure 7B:
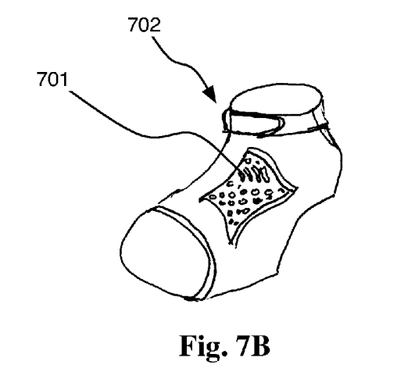
Figure 7C:
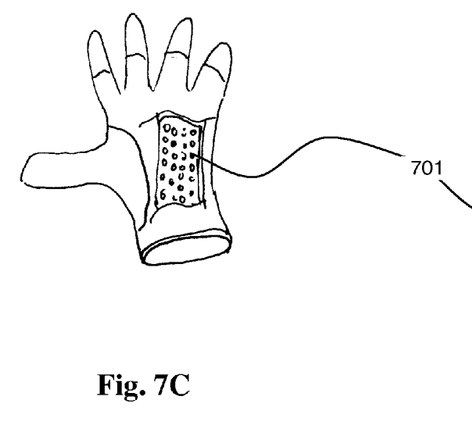
Figure 7D:
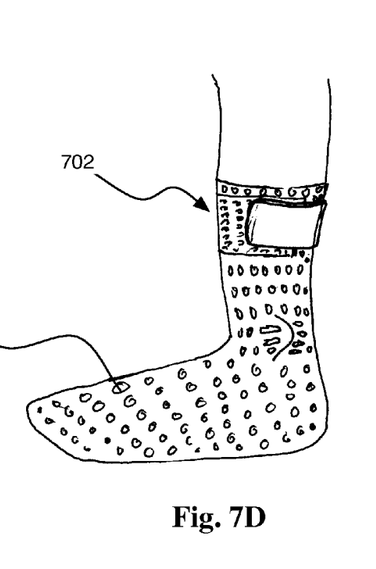

FIGS. 7A-7D illustrate numerous views that show the material as used in various contexts. FIG. 7A for instance shows the material used in conjunction with a shoe. FIG. 7B, shows the material used in conjunction with an ankle support. FIG. 7C illustrates use in conjunction with a glove. FIG. 7D illustrates the invention as a sock. The rectangular perforated portions signify cuts to the shoes, ankle support and glove that may or may not be utilized in the final product. In this manner, the final product may have cut-away areas to increase air flow, or may not have cut-away areas, in case the tubular embodiments reside out of view, within the respective product.

Figure 6:
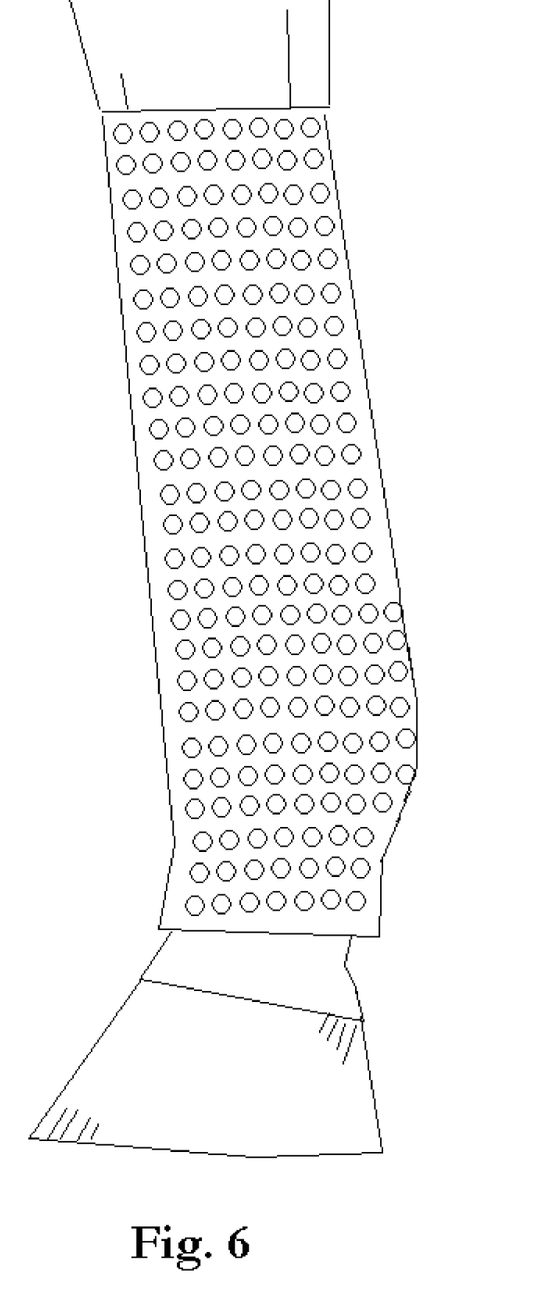
FIG. 6 illustrates an embodiment of the invention for use as an equestrian leg wrap.

FIG. 5 shows an embodiment of the invention which has use as a saddle pad for horses and other animals. By cooling the pad before placement under a horse saddle for instance, the pad can provide a refreshing sensation to the animal. It is also possible to wrap smaller pieces around an animal's leg, either after a race, or after injury. FIG. 6 depicts an embodiment of the invention configured as an equestrian leg wrap. The material is wrapped around the treatment area after being cooled to a desired treatment temperature. The material cools the treatment area while allowing the animal to freely move. The area under the material is highly aerated and this allows the animal to further cool itself via evaporative cooling effects due to sweating. Also, the perforations keep the material from sliding around by increasing the grip of the material on the treatment area. The perforations further maintain the grip by not allowing excess sweat to build up. The material allows the horse to recover faster and this allows the animal to undergo more frequent training sessions for longer periods of time. In addition, the material absorbs impact and provides support for tendons and joints in addition to acting as a cold compress.

Figure 4:
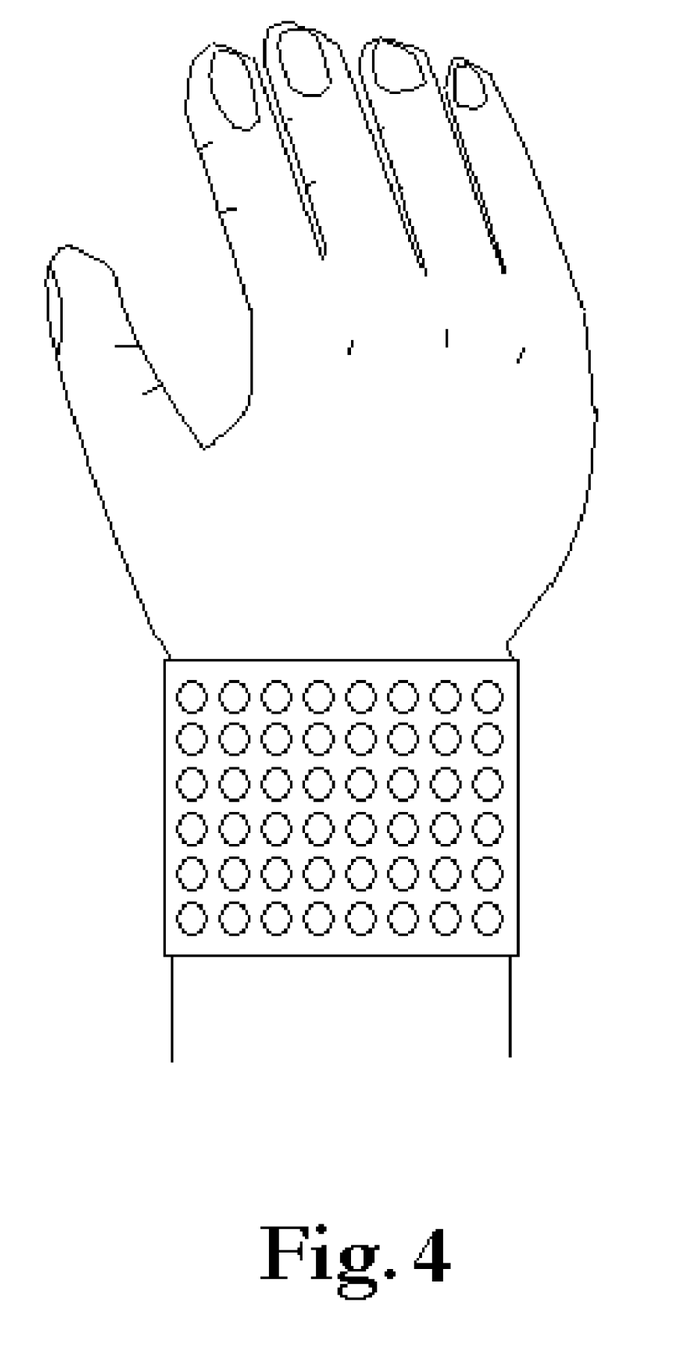
FIG. 4 illustrates an embodiment of the invention for use as a wrist pad.

FIG. 4 depicts an embodiment of the invention either cut from a larger piece to fit the treatment area, or previously manufactured in a smaller format and wrapped around a human wrist. This embodiment provides a padding effect and is suitable for someone with Carpal Tunnel syndrome or other forms of wrist discomfort. When used in the manner depicted, the material cools the wrist while simultaneously aerating and padding the wrist thereby easing any discomfort suffered by the wearer. This embodiment may take the form of a glove.

The material also has applications in other medical arenas and can, for instance, provide a soothing compressive, yet aerating wrap for limiting the amount of swelling and bruising caused after surgery or other forms of injury.

Thus a thermal compressive aerating material and methods of use relating to same is described. The claims, however, and the full scope of any equivalents are what define the metes and bounds of the invention.

What is claimed is:

1. A tubular compressive heating and cooling device configured to enable application of compressive force to an appendage while simultaneously aerating said appendage, said material comprising:
    a flexible tubular element comprising an inner surface configured to contact a treatment area of a subject, wherein said flexible tubular element comprises an elastomer based substance comprising a heat capacity configured to retain alterations in temperature and to effectuate a change in temperature to said treatment area;
    a plurality of perforations protruding through said flexible tubular element wherein said plurality of perforations is configured to allow airflow from said treatment area through said flexible tubular element to aerate said treatment area; and
    inserts into said flexible tubular element to enable a subject wearing said flexible tubular element to change the shape of said flexible tubular element,
    wherein said plurality of perforations increases an elasticity of said flexible tubular element, and
    wherein said plurality of perforations increases a traction of said inner surface against said treatment area.

2. The tubular compressive heating and cooling device according to claim 1 further comprising:
    a housing for said elastomer based substance.

3. The tubular compressive heating and cooling device according to claim 2 wherein said housing comprises a shoe.

4. The tubular compressive heating and cooling device according to claim 2 where said housing comprises a medical device.

5. The tubular compressive heating and cooling device of claim 2 wherein said housing comprises apparel.

6. The material according to claim 1 wherein said elastomer further comprises a chemical configured to alter a color of said elastomer based on a temperature of said elastomer.

7. The tubular compressive heating and cooling device according to claim 1 wherein a size of said tubular element is varied through a sizing element.

8. The tubular compressive heating and cooling device according to claim 6, wherein said temperature is within a range suitable for a specific treatment.

\* \* \* \* \*

UNITED STATES PATENT AND TRADEMARK OFFICE
CERTIFICATE OF CORRECTION

| | | |
|---|---|---|
| PATENT NO. | : 7,959,592 B2 | Page 1 of 1 |
| APPLICATION NO. | : 12/060052 | |
| DATED | : June 14, 2011 | |
| INVENTOR(S) | : Weinberg et al. | |

It is certified that error appears in the above-identified patent and that said Letters Patent is hereby corrected as shown below:

Title page in Related U.S. Application Data insert

Item -- (60)  This application claims benefit of 60/970,887, filed on September 7, 2007 and is a continuation-in-part of 10/848,963, filed on May 19, 2004, now U.S. Patent No. 7,351,217 which claims benefit of 60/310,215, filed on May 23, 2003. --

Signed and Sealed this
Twenty-second Day of November, 2011

David J. Kappos
*Director of the United States Patent and Trademark Office*